United States Patent [19]

Broshears

[11] 4,130,008
[45] Dec. 19, 1978

[54] DEVICE FOR MEASURING FRICTION AND DISTANCE

[76] Inventor: Robert W. Broshears, Rte. 1, Box 1437, Bremerton, Wash. 98310

[21] Appl. No.: 874,884

[22] Filed: Feb. 3, 1978

[51] Int. Cl.² .......................................... G01N 19/02
[52] U.S. Cl. ............................................ 73/9; 73/146
[58] Field of Search ........................ 73/9, 10, 146, 7, 8

[56] References Cited

U.S. PATENT DOCUMENTS

| | | | |
|---|---|---|---|
| 2,225,140 | 12/1940 | Walker | 73/9 |
| 2,496,405 | 2/1950 | Foufounis | 73/9 |
| 3,195,342 | 7/1965 | Bartelink | 73/9 |
| 3,301,039 | 1/1967 | Kummer | 73/9 |
| 3,367,170 | 2/1968 | Lynch | 73/9 |
| 3,538,742 | 11/1970 | Benning | 73/9 |

*Primary Examiner*—S. Clement Swisher
*Assistant Examiner*—Denis E. Corr
*Attorney, Agent, or Firm*—Christensen, O'Connor, Johnson & Kindness

[57] ABSTRACT

A device for measuring the coefficient of friction between a test material and a surface comprises a frame upon which is slidably mounted a test pad holder. The test pad holder has a pad of test material mounted on it so that the test material is in contact with the surface whose coefficient of friction is to be measured when the test pad holder is mounted on the frame. A fillable container fits into the test pad holder, which container is filled with particulate material to thereby provide a force on the test pad in a direction normal to the surface whose coefficient of friction is to be measured. The test pad holder abuts an actuator shaft connected to a piston, which piston abuts a flexible diaphragm that forms one wall of a fluid filled chamber. When the frame is pulled, the test pad holder slides relative to the frame and pushes against the actuator shaft. The actuator shaft in turn urges the piston against the flexible diaphragm, resulting in an increase in pressure within the fluid filled chamber. The increase in pressure is indicated by a pressure gauge fluidly connected to the chamber. As the pulling force applied to the frame is increased, the test pad and holder begin to move relative to the surface. The force required to start the test pad and holder moving relative to the surface, and the force necessary to keep the test pad and holder in motion, as indicated by the pressure gauge, are used to determine the coefficient of friction between the test pad and the surface. The test and holder with test pad attached is easily removable and replaceable and a plurality of holders, each with a test pad of a specific test material, are made available for use. In combination with the above-described apparatus, there is mounted on the frame a device to determine and indicate the distance which the frame travels over the surface whose coefficient of friction is being tested.

15 Claims, 10 Drawing Figures

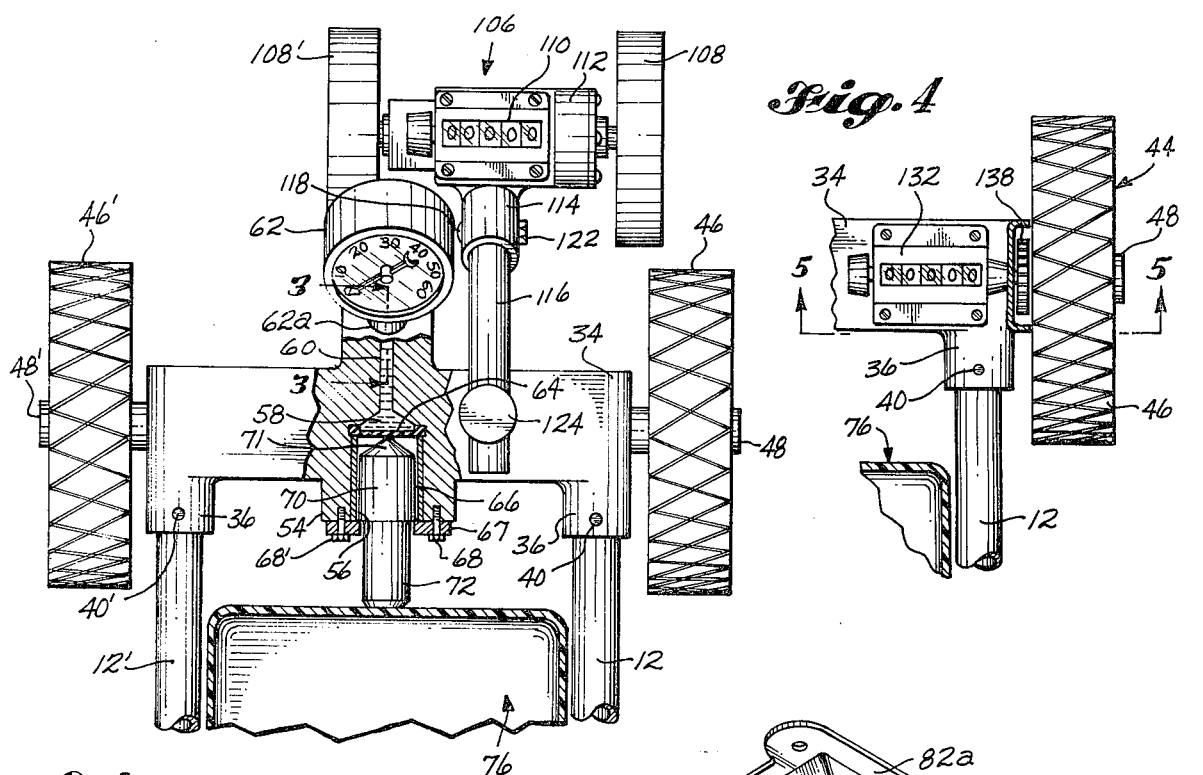
Fig. 2
Fig. 4
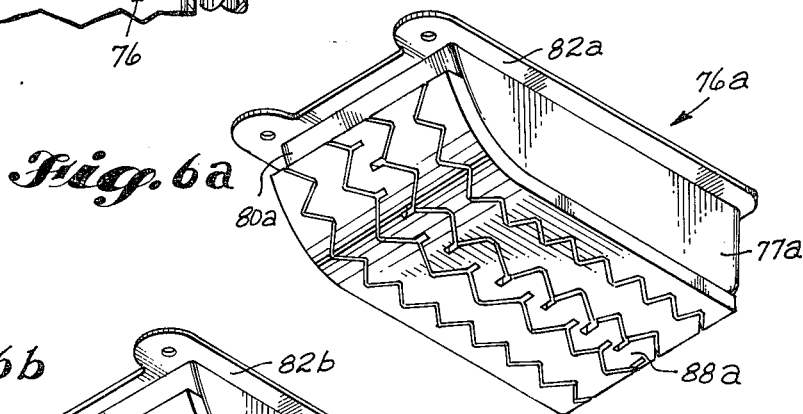
Fig. 6a
Fig. 6b
Fig. 6c
Fig. 5

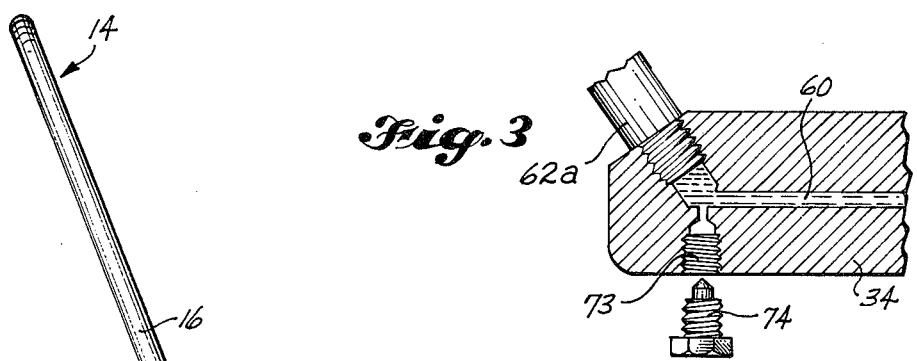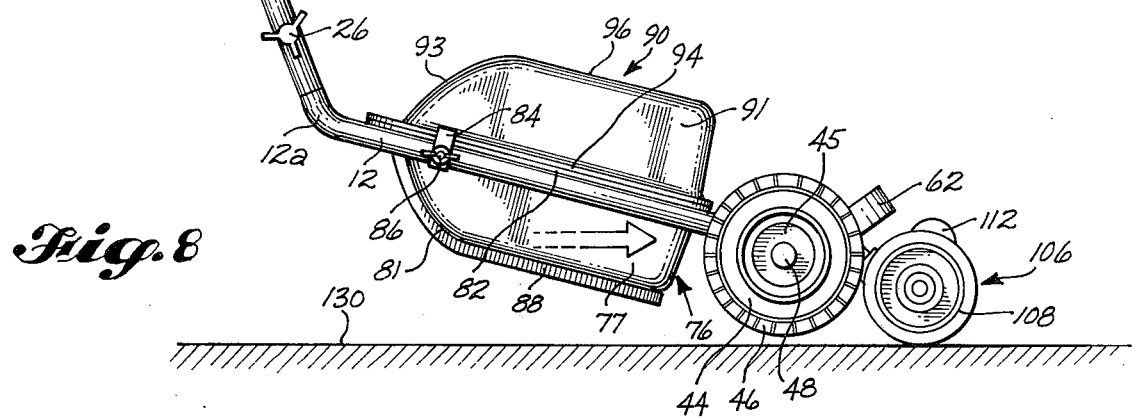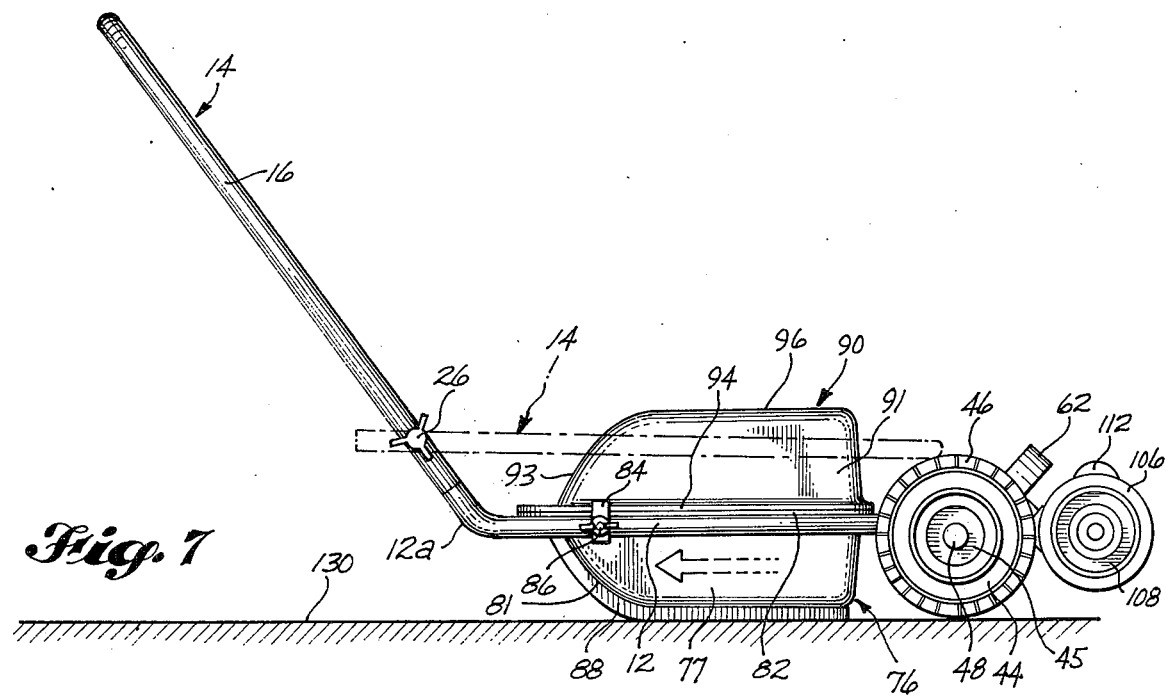

DEVICE FOR MEASURING FRICTION AND DISTANCE

BACKGROUND OF THE INVENTION

This invention relates to measurement devices and, more particularly, to a device for measurement of the coefficient of friction and for measurement of distance.

There are many situations in which it is desired to determine the coefficient of friction between a given material and a given surface. These measurements are used to test the skid resistance of floor coverings and flooring materials, and are also extensively used in automobile accident investigation and reconstruction by police agencies and insurance companies among others.

Since the coefficient of friction of a surface is a function of the material which is engaging the surface, it is desirable for a friction measuring device to have the capability of easily changing the test material being used. This is particularly true in accident investigation where it is necessary to match the test material to the actual tread pattern and wear of the tires on the vehicle involved in the accident.

Also, it has been found that for certain materials there is an optimum normal force which should be used to measure the coefficient of friction in order to achieve an accurate figure. It is desirable, therefore, to have a measuring device, the test weight of which is variable over a given range.

In the accident investigation environment it is often necessary to use the data measured by a friction measuring device as evidence in a court of law. It is therefore desirable to have a device of simple operation such that measurements gathered by the device can be readily verified as accurate and acceptable as evidence in court.

Since accident reconstruction is accomplished in part by determining how far a car skidded, as well as the friction of the road surface, it is desirable to incorporate a distance measuring device with a friction measuring device. Since the investigation of an accident is carried on at the scene, it is desirable to have a device which is easily portable.

It is therefore an object of this invention to provide a friction measuring device.

It is a further object of this invention to provide a friction measuring device in which the test weight and the test material can be varied.

It is still a further object of this invention to provide a friction measuring device, the measurements of which are accurate and can be verified for use as evidence in a court of law.

It is another object of this invention to provide a distance measuring device in combination with the above mentioned friction measuring device.

It is a further object of this invention to provide a friction and distance measuring device which is simple to use, relatively inexpensive to manufacture and easily portable.

SUMMARY OF THE INVENTION

In accordance with the foregoing objects and other objects that will become apparent to one of ordinary skill in the art after reading the following specification, the present invention provides an improved device for measuring the coefficient of friction between a test material and a surface. Broadly, the device includes a test pad holder for holding the test material whose coefficient of friction with the surface is to be measured. A fillable container is adapted to be removably assembled with the test pad holder. The assembled test pad holder and fillable container are slidably and removably mounted on a frame, the frame having a longitudinal dimension and a transverse dimension, so that the assembled test pad holder and fillable container are free to move along the longitudinal dimension of the frame. Handle means are attached to the frame to control movement of the frame.

Also mounted on the frame are force measuring means that measure the magnitude of a force applied to the handle means. The force measuring means has actuator means operatively associated with it and the force measuring means and actuator means are oriented on the frame such that the actuator means abuts the assembled test pad holder and fillable container.

In operation, the fillable container is filled with a substance that will increase its weight. The container is then assembled with the test pad holder and the assembled test pad holder and container are placed on the frame and the test material is brought into contact with the surface whose coefficient of friction is to be measured. When a force is applied to the handle means to pull the device, the friction between the test material and the surface being tested opposes motion of the assembled test pad holder and fillable container with respect to the surface so that the frame moves relative to the assembled test pad holder and fillable container whereby the force measuring means measures the force being applied to the handle. As the force applied to the handle is increased, the force at some point overcomes the friction holding the assembled test pad holder and fillable container stationary with respect to the surface being tested.

The force needed to just begin moving the assembled test pad holder and fillable container relative to the surface can be used along with the normal force provided in part by the weight of the fillable container to determine the coefficient of standing friction between the test pad and the surface by using the well known equation $$F = m \times N$$

or $$m = F \div N$$

where m is the coefficient of friction;

F is the force necessary to overcome friction (pulling force on the handle); and, N is the force normal to the surface (weight of the assembled test pad holder and fillable container).

Once the assembled test pad holder and fillable container are moving with respect to the surface, the coefficient of sliding friction can be obtained using the same formula.

In a preferred embodiment of the invention, a distance measurement device is attached to the frame to enable a measurement of distance travelled over the surface being tested to be made as desired.

It will be appreciated from the foregoing that a new and improved device for the measurement of coefficient of friction is provided. The coefficient of friction is measured by application of the basic friction equation and is simple to use. The weight is provided by a fillable container which can be emptied, thereby making the device lightweight and easy to transport. The test pad holder for holding the test pad is readily removable and replaceable and a plurality of holders can be provided with various test materials attached to allow the operator a choice of test pad materials for use in the friction measurement.

BRIEF DESCRIPTION OF THE DRAWINGS

A better understanding of the objects and advantages of the present invention can be derived by reading the ensuing specification in conjunction with the accompanying drawings wherein:

FIG. 2 is a plan view in partial cross section of the rear portion of the device of FIG. 1.

FIG. 3 is a sectional view along the line 3—3 in FIG. 2.

FIG. 4 is a plan view of a portion of the device shown in FIGS. 1 and 2 showing an alternate means of attaching a distance measuring device.

FIG. 5 is a sectional view along the line 5—5 of FIG. 4.

FIGS. 6a, 6b and 6c are isometric views of test pad housings made in accordance with the present invention with three different test pad materials.

FIG. 7 is a side elevational view of one embodiment of the present invention being used to measure friction.

FIG. 8 is a side elevational view of one embodiment of this invention being used to measure distance.

DETAILED DESCRIPTION OF THE PREFERRED EMBODIMENT

Figure 1:
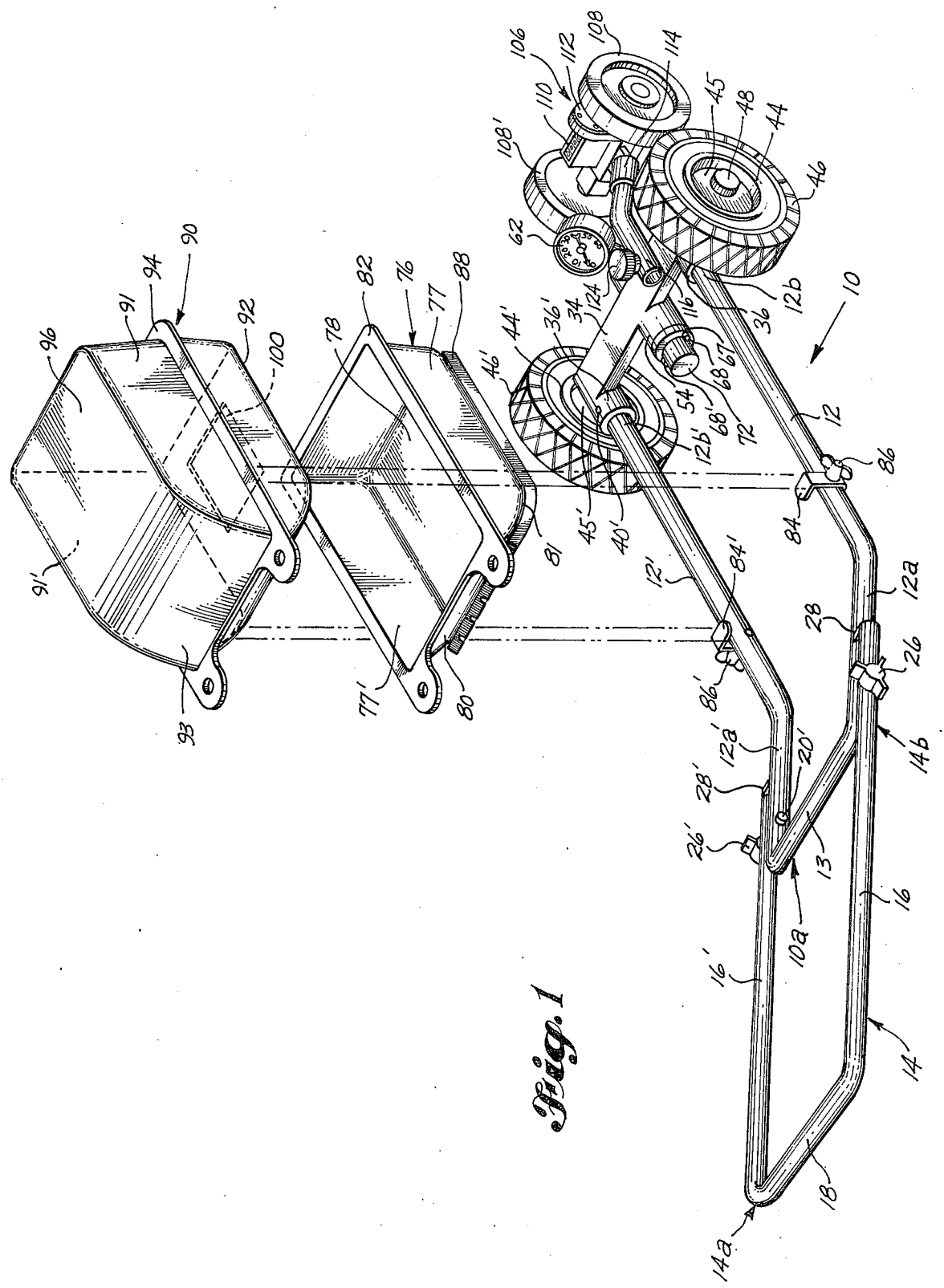
FIG. 1 is an exploded perspective view showing the elements of one embodiment of the invention.

FIG. 1 shows a preferred embodiment of a friction and distance measuring apparatus made in accordance with the present invention. The apparatus comprises a two wheel cart including a generally rectangular frame 10 which is formed in part by two elongate, tubular frame members 12 and 12' in generally parallel, spaced relation. An integral tubular bridge portion 13 is attached to first ends 12a and 12a' of the frame members 12 and 12' transverse to the frame members, forming a first end 10a of the frame 10. The ends 12a and 12a' are bent slightly upwardly.

A handle 14 comprises an elongate tubular member formed into two parallel, spaced legs 16 and 16' and an integral transverse bridge 18. Transverse bridge 18 forms a first end 14a of the handle 14. The second end 14b of the handle 14 is attached to the first end 10a of the frame 10. Each of the legs 16 is in parallel juxtaposition with the first ends 12a and 12a' of its associated tubular frame member 12 or 12'. Each of the legs 16 is secured to its associated tubular frame member 12 or 12' by means of bolts 20 and 20' which pass through diametrically opposed anchoring holes formed in the walls of legs 16 and 16', respectively, near the second end 14b of the handle 14 and through holes formed in the walls of the tubular frame members 12 and 12', respectively. The bolts are held in place by wing nuts 26 and 26' which threadably engage the bolts 20 and 20' respectively. When the wing nuts 26 and 26' are loosened, the handle 14 is free to pivot about the bolts 20 and 20', the handle 14 can be folded to a position generally parallel to the frame members 12 and 12'. The folded arrangement of the handle 14 provides a more compact unit, thereby increasing the portability of the friction-distance measuring apparatus.

Each of the handle members 16 and 16' has a keeper 28 and 28', respectively, fastened to it near first ends 16a and 16a' adjacent the frame members 12 and 12'. The keepers 28 and 28' are cubes of material, preferably plastic, having an elongate indentation which conforms to the shape of the tubular frame members 12 and 12'. When the handle 14 is in position for the operator to pull the frame 10, the handle members 16 and 16' are parallel to the upwardly bent first ends 12a and 12a'. The frame members 12 and 12' engage the indentation in the keepers 28 and 28'. When the wing nuts 26 and 26' are tightened, the frame members 12 and 12' are held tightly against the indented portion of the keepers 28 and 28', whereby the keepers 28 and 28' provide support to prevent the handle 14 from folding until the wing nuts 26 and 26' are loosened. The keepers 28 and 28' are fastened to the handle members 16 and 16' by appropriate means, such as bolts, rivets or adhesive.

The second end 10b of the cart 10 is formed by a measuring platform 34 which is attached to each of the second ends 12b and 12b' of the tubular frame members 12 and 12'. The measuring platform 34 is oriented transversely to the tubular frame members 12 and 12' and is generally in the shape of an elongate, rectangular parallelepiped. The measuring platform 34 is attached to each of the tubular frame members 12 and 12' by a platform coupling 36 and 36' respectively located at each end of the measuring platform 34.

The platform couplings 36 and 36' are cylindrical in shape and integrally formed with the platform 34. Each platform coupling 36 and 36' is oriented such that its longitudinal axis is parallel to the elongate dimension of its associated tubular frame member 12 and 12'.

Each platform coupling 36 and 36' has an aperture formed in the surface thereof which extends into the platform coupling 36 and 36' and is of a diameter sufficient to allow the second end 12b and 12b' of the associated tubular frame member 12 and 12' to be inserted therein. Each of the tubular frame members 12 and 12' is secured in place in its respective coupling 36 and 36' by means of locking pins 40 and 40' which are pressfit into locking holes coaxially formed in the walls of the coupling 36 and 36' and the tubular frame member 12 and 12' such that locking pins 40 and 40' extend through the associated assembled tubular frame member and coupling. The platform 34 and couplings 36 and 36' are preferably cast of a light metal such as aluminum to reduce the overall weight of the apparatus.

Wheels 44 and 44' are rotatably mounted one on each end of the measuring platform 34. The wheels 44 and 44' are preferably of the type adapted to receive a solid rubber tire 46 and 46' respectively. Each of wheels 44 and 44' is attached to its respective end of measuring platform 34 by an axle bolt 48 and 48' respectively which passes through an axle aperture in the associated hub 45 and 45' of the wheels 44 and 44'. The axle apertures are located coaxially with the rotational axis of the wheels 44 and 44'. Each axle bolt 48 and 48' threadably engages a threaded axle mounting hole in the associated end of measuring platform 34. The planes of rotation of the wheels 44 and 44' are parallel to one another and normal to the elongate dimension of the measuring platform 34.

A cylindrical extension 54 is integrally formed in the measuring platform 34 midway between its ends. The longitudinal axis of the cylindrical extension 54 is generally parallel to the longitudinal axes of the platform couplings 36. Referring to FIG. 2, a cylindrical bore 56 is formed in the face of the cylindrical extension 54 and extends into the measuring platform 34. The end of the cylindrical bore 56 within the measuring platform 34 has a conical portion 58 extending from it which in turn opens into the first end of a hydraulic passage 60. The second end of the hydraulic passage 60 is in fluid communication with a pressure gauge, for example, a Bourdon Tube type pressure gauge 62. The pressure gauge has a threaded neck 62a which threadably engages the second end of the hydraulic passage 60.

A flexible diaphragm 64 is mounted within the cylindrical bore 56 and separates the cylindrical bore 56 from the conical portion 58. The diaphragm 64 is mounted so that a fluid seal is formed between the bore 56 and the conical portion 58. The diaphragm 64 is held in place by a sleeve 66 which fits inside the bore 56 adjacent the wall of the bore and extends the length of the bore. The sleeve is held in place by a retainer ring 67 which is mounted on the face of the cylindrical extension 54 and abuts the sleeve 66. The ring is held in place by a pair of machine screws 68 and 68' which threadably engage associated holes in the ring 67 and the cylindrical extension 54. A piston 70 is slidably mounted within the sleeve 66 and bore 56. The piston 70 has a conical end 71 adjacent and abutting the diaphragm 64. The conical end 71 is slightly rounded where it abuts the diaphragm 64 so that it does not puncture the diaphragm. An actuator shaft 72 is attached to the end of the piston 70 adjacent the retaining ring 67. The actuator shaft 72 extends from the piston and passes through an opening in the ring 67. The opening in the ring 67 is too small for the piston 70 to pass through and the piston 70 is therefore held captive within the cylindrical bore 56.

Referring now to FIG. 3, a fill opening 73 is formed in the bottom of the measuring platform 34 and is in fluid communication with the hydraulic passage 60. A suitable hydraulic fluid is placed into the hydraulic passage 60 and in turn into the conical portion 58 in an amount sufficient to fill the passage and conical portion. The fill opening 73 is then closed by inserting a suitable stopper, for example a cone point screw 74, into the fill opening 73.

A test pad holder 76 is in the general shape of an open-topped, hollow parallelepiped having a pair of opposing sidewalls 77 and 77' which are spaced apart by an amount less than the transverse dimension of the frame 10 so that the sidewalls 77 and 77' can fit between the tubular frame members 12, and also having a bottom wall 78 and a first end wall 80. The bottom wall 78 and the first end wall 80 of test pad holder 76 intersect and are curved adjacent to and at their intersection so that a bottom surface 81 of test pad holder 76 is divided into a planar portion (that underlying wall 78), and an adjacent, substantially arcuate portion which is inclined with respect to the planar portion. A flange 82 extends outwardly from at least the sidewalls 77 at the upper edge of the test pad holder 76 in a plane parallel to the planar portion of bottom surface 81 so that the test pad holder 76 can be mounted on the frame 10 with flange 82 resting on tubular frame members 12 and 12'. The test pad holder 76 may then be slid towards measuring platform 34 along the frame members 12 and 12'.

A test pad 88, constructed of whatever material is to be used to determine the coefficient of friction, is mounted on the bottom surface 81 of test pad holder 76 and is fastened by a suitable means, such as an adhesive or rivets. When the test pad holder 76 is mounted on the frame 10, the end wall 80 faces the first end 10a of the frame 10. The bottom surface 81 allows the test pad 88 to approximate a configuration similar to that of a locked, skidding automobile wheel on the surface whose coefficient of friction is being measured. This provides an increased accuracy in the friction measurement made in an automobile accident investigation. Secondarily, the arcuate portion prevents the end of the test pad 88 from peeling away from the test pad holder 76 under the force of friction as the test pad 88 is dragged across the surface whose coefficient of friction is being measured.

A fillable weight container 90 is generally in the shape of a hollow, rectangular box having a pair of opposing side walls 91 and 91', a bottom wall 92, and a first end wall 93 respectively complimentary to side walls 77, bottom wall 78, and end wall 80 of test pad holder 76, and also having a top wall 96 opposing bottom wall 92. The weight container 90 is adapted to fit inside the test pad holder 76, with side walls 91, bottom wall 92 and end wall 93 respectively abutting side walls 77, bottom wall 78, and end wall 80 of test pad holder 76. The top wall 96 and end wall 93 intersect and are curved adjacent and at their intersection so that a top surface of the weight container 90 is a mirror image of the bottom surface. The purpose of the curvature of the top surface 102 will be explained below. A flange 94 extends outwardly from at least the side walls 91 intermediate bottom wall 92 and top wall 96. When weight container 90 is placed into the test pad holder 76, the flange 94 is coextensive with the flange 82. Brackets 84 and 84' are mounted on the frame members 12 and 12' respectively and held in place by wing head bolts 86 and 86' which pass through threaded holes in the brackets 84 and 84' and abut the frame members 12 and 12'. The brackets 84 and 84' overlie the flanges 82 and 94 and loosely hold the weight container 90 and test pad holder 76 on the frame 10.

The weight container 90 has a fill aperture 100 formed in its bottom wall 92. The fill aperture 100 enables a particulate material such as sand or lead to be placed inside the weight container, thereby increasing its weight. Preferably, the weight material is enclosed in a bag within the weight container. After the weight material is placed inside the weight container 90, the weight container 90 is placed into the test pad holder 76 and the fill aperture 100 is blocked by the bottom wall 78 of the test pad holder 76. By varying the density of the fill material, or by varying the amount of the fill material used, the weight of the weight container 90 can be varied as desired. The weight material can be entirely removed to lessen the weight of the apparatus during transit to and from the measurement location.

A distance measuring device generally denoted as 106 in the drawings is a conventional measuring wheel type of device such as those manufactured by Rolatape Corporation of Los Angeles, California and designated by Rolatape Model Nos. 110 and 112. The distance measuring device 106 has two rotatable distance measuring wheels 108 and 108' which are drivingly connected to an indicator 110 by means of a gear train 112. As the distance measuring wheels 108 and 108' move over a surface, the motion is transmitted to the indicator 110 which provides a readout of the distance travelled by the distance measuring wheels 108 and 108'.

A tubular adapter bar coupling 114 is attached to the distance measuring device 106 at a point midway between the distance measuring wheels 108 and 108'. A tubular adapter bar 116 has an outside diameter slightly smaller than the inside diameter of the tubular adapter bar coupling 114. A first end of the adapter bar 116 is inserted into the adapter bar coupling 114. The adapter bar 116 is secured to the adapter bar coupling 114 by means of a bolt 118 which passes through diametrically opposed holes formed in the walls of the adapter bar 116 and the adapter bar coupling 114. The bolt 118 is held in place by a nut 122. The adapter bar 116 is attached to the measuring platform 34 by means of a large thumbscrew 124 which passes through diametrically opposed holes formed in the walls of the adapter bar 116 near the second end of the adapter bar 116. The thumbscrew 124 threadably engages a hole formed in the upper surface of the measuring platform 34. The distance measuring device 106 is attached to the measuring platform 34 in such an orientation that the plane of rotation of the distance measuring wheels 108 and 108' is parallel to the planes of rotation of the cart wheels 44 and 44'.

An alternate method of providing a distance measuring device is shown in FIGS. 4 and 5. A conventional rotational distance counter 132 is mounted on the measurement platform 34 and oriented so that its rotational axis is parallel to the rotational axis of the wheel 44. A drive gear 134 is mounted on the wheel 44 intermediate the measuring platform 34 and the wheel 44 so that the rotational axis of the drive gear 134 is coaxial with the rotational axis of the wheel 44. The drive gear 134 is affixed to the wheel 44 so that as the wheel rotates, the drive gear 134 rotates. The drive gear 134 drivingly engages an intermediate gear 136 which is rotatably mounted on a shaft 138 which extends from the measuring platform 34 parallel to the rotational axis of the drive gear 132. The intermediate gear 136 in turn drivingly engages a counter shaft gear 138 which is affixed to the shaft of the distance counter 132. The gear arrangement is such that as the wheel 44 moves over a surface, the motion is transmitted to the distance counter 132 which provides a readout of the distance travelled by the wheel 44.

The operation of a preferred embodiment of an apparatus constructed in accordance with the princples of the present invention for measuring coefficient of friction is shown in FIG. 7. The apparatus is positioned so that the test pad 88 engages a surface 130 whose coefficient of friction is to be measured. The orientation of distance measuring device 106 is such that when the test pad 88 is in full contact with the surface 130, the distance measuring wheels 108 and 108' are not in contact with the surface 130. Alternatively, the distance measuring device 106 could be removed temporarily from the apparatus. A force is applied to the handle 14 to pull the device in a direction as shown by the arrow in FIG. 7. The friction between the test pad 88 and the surface 130 tends to oppose motion of the test pad 88 relative to the surface 130. When the test pad rests on the surface 130, the entire weight of the assembled weight container 90 and test pad holder 76 is supported by the test pad. The flange 82 no longer rests on the frame 10 so that the frame 10 moves in the direction of the applied force and the assembled test pad holder 76 and weight container 90 move relative to the frame in a direction opposite the applied force, with the test pad holder 76 remaining stationary relative to the surface 130. The movement of the frame 10 relative to the mated test pad holder 76 and weight container 90 causes the actuator shaft 72 to abut the end of wall 79 of the test pad holder 76. As force continues to be applied to the handle 14, the frame 10 continues to move relative to the mated test pad holder 76 and weight container 90 and the actuator shaft 72 is pushed in a direction opposite the direction of motion of the frame 10. The movement of the actuator shaft 72 forces the piston 70 further into the cylindrical bore 56, thereby urging the conical end 71 against the flexible diaphragm 64. The distortion of the diaphragm 64 increases the pressure of the hydraulic fluid within the conical portion 58 and the passage 60. The increase in pressure is indicated on the pressure gauge 62 and is of a magnitude substantially equal to the magnitude of the pulling force applied to the handle 14. The diaphragm 64 is made of a substance which is flexible yet which is strong enough so that the portion of the diaphragm surrounding the point of contact with the conical end 71 does not give and balloon out toward the piston 70. Also, the hydraulic fluid must not be of a type which will corrode and weaken the diaphragm 64.

It will be noted that tubular frame members 12 and 12' are bent in a direction away from the surface 130 near the first ends 12a and 12a' of the frame members. The bend in the tubular frame members 12 and 12' allows the operator to have easy access to the handle while remaining erect. Alternatively, the handle 14 could be attached to the frame 10 by some type of pivot arrangement such that the angle of the handle 14 could vary from parallel to the surface 130 to completely vertical to the surface 130.

As the force applied to the handle 14 is increased, it overcomes the force of friction between the test pad 88 and the surface 130, at which time the mated test pad holder 76 and weight container 90 begin to move in relation to the surface 130 in the direction of the applied force. Using the magnitude of the force applied to the handle as indicated by the pressure gauge 62 as the test pad holder 76 just begins to move and the weight of the holder and container assembly, the coefficient of standing friction can be determined using the formula $$F = m \times N$$

or $$m = F \div N$$

where m equals the coefficient of friction;

F equals the force necessary to overcome the friction (the force required to cause the test pad to just begin to move over the surface 130); and N equals the force normal to the surface on which the test pad rests (the weight of the filled weight container 90 and the assembled test pad holder 76).

Since the coefficient of sliding friction is less than the coefficient of standing friction, the force required to keep the test pad holder 76 moving over surface 130 will be less than the force which was required to begin the movement. The decrease in force will be registered as a decrease in pressure in the cylindrical portion 58 and passage 60 as indicated by the pressure gauge 62. The coefficient of sliding friction can be obtained by continuing to apply force sufficient to keep the test pad holder in motion and using the same $$F = m \times N$$

equation.

FIG. 8 shows an apparatus built in accordance with the principles of the present invention being used to measure distance. The apparatus is lifted by handle 14 so that the test pad 88 and the platform wheels 44 and 44' are no longer in contact with the surface 130. A force is applied to the handle 14 to push the apparatus in the direction indicated by the arrow. The distance traveled by the distance measuring wheels 108 and 108' can be read from the indicator 110.

In the investigation of an accident, the investigator desires to determine the speed at which the car (or cars) involved in the accident was traveling prior to the time of the accident. The speed can be determined in many cases by measuring the skid marks produced by the tires of the car so long as the investigator knows the coefficient of friction of the road surface. Tests made using the device of the present invention to determine coefficient of friction have shown that the error in computed speed using the data gathered by this invention when compared with actual speeds of cars performing test skids ranged from 0 miles per hour to several miles per hour over a range of 0 to 30 miles per hour.

It is not possible to accurately measure coefficient of friction for speeds greater than 30 miles per hour and relate them to stopping distance as shown by skid marks because of the effect on skid marks of tire heating during skids from speeds above 30 miles per hour. However, a reduced coefficient of friction can be approximated by adjusting the measured coefficient of friction proportionally to the total length of the skid.

FIGS. 6a, 6b and 6c show a plurality of test pad holders 76a, 76b and 76c with the test pads 88a, 88b and 88c attached. The test pad 88a is made of rubber of the type used to make automobile tires, with a tread pattern formed therein. The test pad 88c is also made of tire rubber and has a second specific tread pattern formed in it. The test pad 88b is made of tire rubber and has no tread pattern, simulating a worn or bald tire. The various test pads illustrate a portion of the test pad types which can be made available to an accident investigator for use with an apparatus constructed according to the principles of the present invention. The investigator can choose the test pad which best approximates the tread pattern on the tires of the cars involved in an accident. It is even possible that a portion of the tire of the cars actually involved could be removed and used as a test pad. The ease of removal of the test pad holder 76 from the frame 10 makes it an easy matter for the investigator to switch from one test pad type to another. By having the top surface 102 of the weight container 90 curved to match the bottom surface 81 of the test pad holder 76, the extra test pad holders can be stacked on the weight container 90 during storage and transit.

It is possible that the apparatus disclosed by the present invention could be used in environments other than automobile accident investigation in which case the test pad holders could be constructed with test pads of various materials such as shoe leather or floor covering attached, depending upon the exact testing environment in which the apparatus was to be used.

It has also been determined in tests using this invention that certain magnitudes of weight give optimum results depending on the composition of the surface whose coefficient of friction is being measured. For example, the weight of 20 pounds has been found to be optimum for a measurement on a paved highway, while a weight of 40 pounds is optimum on a gravel road surface. These figures are mentioned by way of example only and are not intended to limit the scope of the invention to those ranges. The nature of the weight container of the present invention allows for easy variation of the test weight used by simply adding or removing a quantity of fill material or substituting a lighter or heavier fill material for the one being used. The fillable nature of the weight container 90 of the present invention also enables the weight material to be removed prior to transporting the apparatus from one testing location to another, thereby providing a lighter weight apparatus.

It will be appreciated that a friction measuring device is provided which uses a basic application of the equation $$F = m \times N$$

to determine the coefficient of friction. The simple operation of the device disclosed by this invention makes for easy verification of data gathered through its use for use as evidence in a court of law. A device built according to the principles of the present invention needs no certification as to accuracy and is self calibrating. In order to take advantage of this self calibration feature using the preferred embodiment hereinbefore described, the distance measuring device is removed and the apparatus is stood up on cart wheels 44 and 44' so that the longitudinal axis of the actuator shaft 74 is vertical. The filled weight container 90 and the test pad holder 76 are allowed to rest on the actuator shaft 72 and a reading is taken from the pressure gauge 62 which preferably is calibrated in pounds. The reading obtained represents the weight (N) of the assembled weight container 90 and test pad holder 76. During operation of the apparatus, the force needed to overcome friction (F) is read from the same pressure gauge 62 as the weight reading previously obtained. Since a comparison of forces is used to determine the coefficient of friction rather than absolute values of force, any error in the pressure gauge 62 is cancelled out by use of the same gauge for both measurements. When the apparatus is in the friction measuring position, the entire weight of the weight container and test pad holder 76 is on the test pad 88. The flange 82 does not contact the frame 10 and none of the weight is distributed through the frame 10. Likewise, none of the weight of the frame 10 or wheels 44 and 44' is distributed through the weight container 90 and test pad holder 76.

While a preferred embodiment of the invention has been illustrated and described, it will be appreciated by those skilled in the art and others that various changes can be made herein without departing from the spirit and scope of the invention.

The embodiments of the invention in which an exclusive property or privilege is claimed are defined as follows:

1. A device for measuring coefficient of friction comprising:

a test pad of material, the coefficient of friction of which is to be measured on a given surface;

a test pad holder for holding said test pad in contact with said surface;

a frame upon which said test pad holder is slidably and removably mounted, said frame having a longitudinal dimension and a transverse dimension, said test pad holder being free to slide on said frame along the longitudinal dimension of said frame, said frame including a pair of elongate first frame members in parallel spaced relation and extending in said longitudinal dimension of said frame, each of said first frame members having a first end and a second end and further including an elongate second frame member transverse to said first frame members and attached to a first end of each of said first frame members;

container means adapted to fit inside said test pad holder, said container means having an aperture therein through which a fill material can be placed into said container means to increase the weight of said container means to a predetermined magnitude;

at least one wheel rotatably mounted on each end of said second frame member, the plane of rotation of said wheel being normal to the elongate dimension of said second frame member, said wheels being of diameter sufficient to allow said test pad to engage said surface;

handle means for controlling the movement of said frame, said handle means being attached to a second end of each of said first frame members;

a chamber affixed to said second frame member, said chamber including a first portion and a second portion;

a flexible diaphragm, mounted within said chamber and forming a fluid barrier between said first portion and said second portion, said second portion being a closed hydraulic chamber;

a piston slidably mounted within said first portion, said piston having a first end and a second end, said first end of said piston abutting said flexible diaphragm;

an actuator having a first end and a second end, said first end of said actuator being affixed to said second end of said piston and said second end of said actuator abutting said test pad holder such that motion of said test pad holder relative to said frame along the longitudinal dimension of said frame in the direction away from the handle means causes said test pad holder to move said actuator which in turn moves said piston so as to cause an increase in pressure in said second portion; and, gauge means for indicating the magnitude of pressure within said second portion.

2. The device of claim 1 further comprising distance measuring means for measuring distance traveled by said device over said surface, and means for attaching said distance measuring means to said frame.

3. The device of claim 2 wherein said distance measuring means comprises a conventional measuring wheel.

4. The device of claim 2 wherein said distance measuring means comprises:
counter means for indicating the distance traveled;
gear train means associated with said frame for drivingly connecting said at least one wheel to said counter means.

5. The device of claim 1 wherein said gauge means comprises a Bourdon tube type gauge.

6. The device of claim 1, wherein said test pad holder has a bottom surface divided into a substantially planar portion and an adjacent, substantially arcuate portion which is inclined with respect to said planar portion, said arcuate portion facing said handle means in assembly, and wherein said test pad is secured to said test pad holder so that said test pad underlies said bottom surface thereof.

7. The device of claim 1, wherein said test pad holder has a flat bottom wall, and a pair of side walls, and at least one end wall integral with and extending from said bottom wall, said at least one end wall facing said handle means in assembly and said pair of side walls being separated from each other by an amount less than said transverse dimension of said frame, and wherein said test pad holder further comprises a flange extending from said pair of side walls for resting upon and supporting said test pad holder from said pair of first frame members.

8. The device of claim 7, wherein said test pad is secured to said bottom wall and to said at least one end wall.

9. The device of claim 8, wherein said at least one end wall arcuately extends from said bottom wall so that a transition between said at least one end wall and said bottom wall is a smooth curve.

10. The device of claim 9, wherein said container means has a container bottom wall and a container end wall integral therewith, which are respectively complimentary to said bottom wall and said at least one end wall of said test pad holder.

11. The device of claim 10, wherein said container means further has a pair of container side walls integral with said container bottom wall and complimentary to said pair of side walls of said test pad holder, said container means further comprising a container flange extending from said pair of container side walls and complimentary to said flange of said test pad holder.

12. The device of claim 11, wherein said container means has a container top wall integral with said pair of container side walls, and wherein said container flange extends from said container side walls intermediate said container bottom wall and said container top wall.

13. The device of claim 1, wherein said test pad holder is in the form of an open-topped, first hollow box, and wherein said container means is also in the form of a second hollow box complimentary to and removably receivable in said first hollow box.

14. The device of claim 1, wherein said handle means comprises an elongate handle member formed into first and second legs each having a first end and a second end, said elongate handle member being further formed into a bridge extending transversely between said first ends of said first and said second legs so as to maintain said first and second legs in parallel, spaced-apart relation, and wherein said handle means further comprises means for removably securing said second ends of said first and second legs to said second ends of said pair of first frame members.

15. The device of claim 14, wherein said second ends of said pair of first frame members extend at an angle with respect to said longitudinal dimension of said frame.

* * * * *